United States Patent
Sprenger-Haus-sels et al.

(10) Patent No.: US 9,410,145 B2
(45) Date of Patent: Aug. 9, 2016

(54) METHOD FOR THE ISOLATION OF NUCLEIC ACIDS

(75) Inventors: Markus Sprenger-Haus-sels, Mettmann (DE); Gaby Schulte, Duesseldorf (DE); Thomas Deutschmann, Wuppertal (DE); Sibylle Felker, Burscheid (DE)

(73) Assignee: QIAGEN GMBH, Hilden (DE)

( * ) Notice: Subject to any disclaimer, the term of this patent is extended or adjusted under 35 U.S.C. 154(b) by 523 days.

(21) Appl. No.: 11/815,296

(22) PCT Filed: Feb. 13, 2006

(86) PCT No.: PCT/EP2006/001274
§ 371 (c)(1),
(2), (4) Date: Feb. 25, 2008

(87) PCT Pub. No.: WO2006/084753
PCT Pub. Date: Aug. 17, 2006

(65) Prior Publication Data
US 2008/0207889 A1 Aug. 28, 2008

(30) Foreign Application Priority Data
Feb. 11, 2005 (EP) ..................................... 05002932

(51) Int. Cl.
*C07H 21/00* (2006.01)
*C07H 21/02* (2006.01)
*C12N 15/10* (2006.01)

(52) U.S. Cl.
CPC ........ *C12N 15/1003* (2013.01); *C12N 15/1006* (2013.01)

(58) Field of Classification Search
CPC ......................... C12N 15/1006; C12N 15/1003
See application file for complete search history.

(56) References Cited

U.S. PATENT DOCUMENTS

| 6,383,393 | B1 | 5/2002 | Colpan et al. |
| 6,562,568 | B1 | 5/2003 | Kleiber et al. |
| 6,992,182 | B1 * | 1/2006 | Muller et al. ............. 536/25.41 |
| 7,005,266 | B2 * | 2/2006 | Sprenger-Haussels ........... 435/6 |
| 2006/0172331 | A1 * | 8/2006 | Sprenger-Haussels ........... 435/6 |

FOREIGN PATENT DOCUMENTS

| EP | 1 479 769 A | 5/2004 |
| WO | 9501359 | 1/1995 |
| WO | WO 98/31840 | 7/1998 |
| WO | WO 2006/084753 A1 * | 8/2006 |

OTHER PUBLICATIONS

Smith, Lucinda S. et al.; "Increased Yield of Small DNA Fragments Purified by Silica Binding;" Biotechniques, vol. 18, No. 6, 1995, pp. 970-972.
Winters, Michael A. et al., "Plasmid DNA Purification by Selective Calcium Silicate Adsorption of Closely Related Impurities;" Biotechnology Progress, vol. 19, No. 2, Jan. 31, 2003, pp. 440-447.
Third Party Observation based on Publication No. EP1851313; Application No. 06706886; "Method for Isolating Nucleic Acids, The Nucleic Acids Being Immobilised on a Matrix At an Increased Temperature"; filed Aug. 14, 2012.
Qiagen Sample & Assay Technologies, "MagAttract Virus Mini M48 Handbook." Jun. 2012.

* cited by examiner

*Primary Examiner* — Lawrence E Crane
(74) *Attorney, Agent, or Firm* — McBee Moore Woodward Vanik IP, LLC.

(57) ABSTRACT

The present invention concerns an improved method for the isolation of nucleic acids such as DNA and RNA from bacterial, plant, animal or human cells as well as from cell cultures and virus cultures, wherein the nucleic acid is immobilised on a matrix having a silicon-oxygen compound in the presence of a chaotropic agent and an alkanol, carried out in a temperature range of 36° to 75° C.

27 Claims, 2 Drawing Sheets

METHOD FOR THE ISOLATION OF NUCLEIC ACIDS

CROSS REFERECE TO RELATED APPLICATIONS

This is a §371 National Stage Application of International Application No. PCT/EP2007/01274 filed Feb. 13, 2006, which claims priority from EP 05002932.1 filed Feb. 11, 2005.

BACKGROUND OF THE INVENTION

1. Field of the Invention

The present invention concerns an improved method for the isolation of nucleic acids.

2. Description of Related Art

The isolation of nucleic acids such as DNA and RNA from plant, animal or human cells as well as from cell cultures or virus cultures is normally carried out according to a uniform basic pattern: the starting materials containing the nucleic acids are first digested—in part with the use of protein-degrading enzymes. The individual components can then be separated in subsequent steps by many different methods.

The separation of the protein fraction inevitably present in every cell lysate embodies here a particularly important step. The separation can be carried out, for example, by bringing the protein/nucleic acid mixture into contact with phenol and/or mixtures of chloroform/isoamyl alcohol. The protein fraction can also be precipitated from the aqueous phase by the addition of denaturing salts—such as, for example, guanidinium hydrochloride or guanidinium isothiocyanate. In addition the proteins can be degraded by the addition of proteases and then removed. Finally the unwanted nucleic acid can be separated by the selective addition of DNase or RNase and the respectively desired nucleic acid fraction can be obtained. However, to protect the nucleic acids from unwanted enzymatic degradation during the isolation procedure, work must be carried out under sterile and nuclease-free conditions. The separation of nucleic acids can also be carried out by ultracentrifugation.

Most of the methods known from the prior art are based on one of the following two separation principles:

The "classical methods" are based on a single stage process in which after addition of a buffer, which in most cases contains a guanidinium salt, and after addition of an organic extraction agent—mostly chloroform or phenol—an extraction is carried out. The undesirable attendant materials are then rejected with the organic phase. The nucleic acids remaining in the aqueous phase can then be separated by a phase separation and isolated.

The main disadvantage of this method is that in addition to the use of toxic and health-hazardous materials—such as guanidinium isothiocyanate, phenol or chloroform, water-soluble materials remain in the aqueous nucleic acid solution as impurities, which must be separated in additional, very time-consuming purification steps. This problem complicates the use of this method for the isolation of nucleic acids from plants, for example, since these mostly contain considerable amounts of polysaccharides and similar water-soluble substances.

In view of these disadvantages an alternative method has become established in the prior art which is based on the selective adsorption of nucleic acids onto solid, usually mineral, carriers such a silicon dioxide. Here, in a multi-stage procedure different buffer solutions (lysis, binding, washing and elution buffers) are added sequentially to the cell or virus lysate; in the final step the purified nucleic acid is eluted from the carrier.

Meanwhile expert circles have investigated the physicochemical principle of the binding of nucleic acids to mineral carriers in the presence of chaotropic salts. It was postulated that the binding of the nucleic acid to the surface of the mineral carrier is based on a disruption of the highly ordered structures of the aqueous milieu, through which the nucleic acids adsorb onto the surface of mineral materials, in particular glass and silica particles.

A particular disadvantage of the above-described method is that with the use of samples that are enhanced with a particularly high fraction of spurious secondary materials, considerable losses in yields must be taken into account to achieve the desired high level of purity.

SUMMARY OF THE INVENTION

The object of the present invention is thus to provide a method for the isolation of RNA or DNA that does not have the disadvantages described above and known from the prior art and provides nucleic acids in high yield and purity.

It was surprisingly found that an improvement in the binding of the nucleic acid to silica particles—preferably to magnetic silica particles—can be achieved in the presence of chaotropic agents and/or alcohol, particularly in the presence of chaotropic agents and alcohol, if the solution containing the nucleic acid is heated before or during binding. This improvement is particularly effective for both the binding of viral RNA and DNA and synthetic RNA, and also for other nucleic acid species.

DETAILED DESCRIPTION OF A PREFERRED EMBODIMENT

Figure 1:
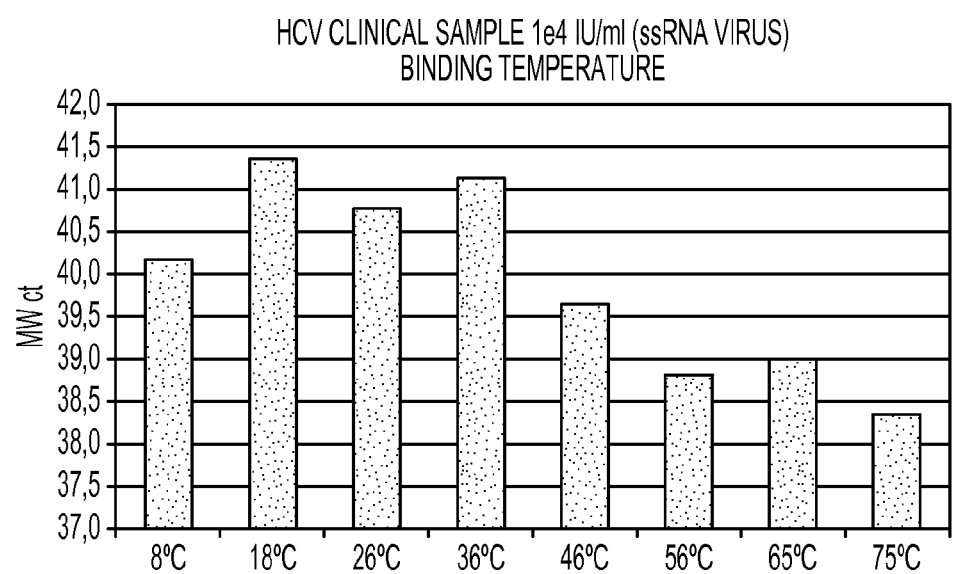
FIG. 1 shows mean values of the Ct values of HCV-RNA after real time (RT)-PCR in relation to the binding temperature. Negative human plasma with HCV (RNA virus) was treated according to the method described at Example 1. Each of 12 replicates of the samples were tempered prior to binding to 8° C., 18° C., 26° C., 36° C., 46° C., 56° C., 65° C. and 75° C., respectively. The eluates obtained were in each case subjected to an HCV-specific real-time (RT)-PCR.

According to the invention biological materials are understood to be materials of particulate or molecular basis. These include in particular, viruses, phages and cells such as, for example, bacteria, but also human, animal (for example leucocytes) or plant cells. In particular, the method according to the invention is suitable preferably for the isolation of nucleic acids such as DNA or RNA from sample material of human or animal origin—such as, for example clinical samples such as blood, plasma, serum, mouth rinses, urine, cerebral-spinal fluid, sputum, stool, punctates, epithelial smears, biopsies and other tissue or bone marrow samples.

The sample can also originate from the area of environmental analysis, food analysis or molecular biology research, for example from bacterial cultures, viral cultures, phage lysates, air or water filters and products from amplification procedures, for example in PCR.

Native or modified biological material can be isolated with the method according to the invention. Native biological material is understood to be material the structure of which has not been irreversibly modified in respect of the naturally occurring biological materials. However, this does not exclude the modification of other components of the sample. If, for example, cells are to be isolated, the medium surrounding the cells can indeed be modified, but not the cells as such. If nucleic acids are to be isolated, these too should be in the native form, i.e. not cut or modified by having reactive groups coupled thereto. Thus, the definition native biological material in particular does not comprise biotinylated nucleic acids. Inter alia viral DNA, viral RNA or cellular nucleic acids from human or animal sample material embody examples of native biological materials.

Modified biological material comprises materials that do not occur in nature, e.g. nucleic acids that are modified by attachment of reactive, detectable or stabilising groups or groups enabling immobilisation, for example biotinylated nucleic acids; in addition synthetic DNA and RNA as well as, for example, 'armored RNA' can be mentioned.

In certain cases the sample can be used without pre-treatment in the method according to the invention. In many cases, however, the sample should be digested by a suitable method and the biological material contained in the sample be released. Methods for digesting samples are known to the person skilled in the art and can be chemical, enzymatic or physical in nature. A combination of these methods is also possible.

Within this context different methods can appear to be more beneficial for different biological materials, but on the other hand any of the following methods is suitable in principle: lysis with the aid of ionic and non-ionic surfactants such as, for example, SDS, LiDS or Sarcosyl in suitable buffers, the use of chaotropic salts such as, for example, guanidine hydrochloride, (GHCl), guanidine thiocyanate (GTC), sodium iodide, sodium perchlorate, etc.; mechanical disintegration, such as, for example, by means of a French press, ultrasound, milling with glass spheres, aluminium or in liquid nitrogen; enzymatic lysis, for example with lysozyme, proteinases, pronases or cellulases, or another of the commercially available lysis enzymes; lysis of the cells with bacteriophages or virus infection; freeze drying; osmotic shock; microwave treatment; temperature treatment, for example warming or heating or freezing, e.g. in dry ice or liquid nitrogen and thawing; alkali lysis.

As already stated above, all the above methods represent standard techniques for lysis that are adequately known in the prior art, and any of the methods or their combination can be used.

Thus, a combination of chaotropes and surfactants is particularly effective for the lysis of bacterial cells. An exemplary, suitable agent for the lysis thus comprises a chaotrope such as, for example, GTC or GHCl and a detergent such as, for example, SDS or Sarcosyl. These lysis agents can be present in aqueous solution or in a buffer solution, that is as so-called lysis buffers. Any suitable buffer can be used as buffer such as, for example, Tris, Bicin, Tricin or phosphate buffer. Alternatively, the lysis agent can also be added separately. Suitable concentrations and amounts of the lysis reagent vary according to the respective system, type of cell, etc., and can be determined by the person skilled in the art wherein, for example, concentrations in the range of 2 M to 7 M chaotrope such as, for example, GTC, GHCl or sodium iodide or sodium perchlorate, 0.1 M to 1 M alkaline reagent such as, for example, NaOH, and 0.1 to 50 wt % (weight/volume) detergent can be used. An example of such a lysis buffer thus contains an aqueous solution of 4 M GTC and 1% (weight/volume) Sarcosyl.

Different incubation conditions can be suitable for different lysis systems and are known from the prior art. For a lysis buffer containing a detergent and/or a chaotrope the incubation can be carried out, for example, at room temperature or at elevated temperature, for example in a range from 37 to 65° C.

Similarly, the incubation time can also vary, from a few minutes to up to 24 hours, for example 5 minutes up to 2 hours. In the case of the GTC/Sarcosyl lysis buffer and bacterial cells, an incubation at, for example, 65° C. for 10 to 20 minutes has proved to be advantageous, but can also be varied as required. For enzymatic lysis with, for example, proteinase K etc., longer treatment times can be necessary, for example over a period of 12 hours.

Lysis is preferably carried out in the presence of chaotropic salts wherein the concentration of these salts is between 2 and 8 mol/l, preferably 4 to 6 mol/l. Chaotropic salts are, for example, sodium iodide, sodium perchlorate, guanidinium thiocyanate, guanidinium isothiocyanate or guanidinium hydrochloride. Binding is not, however, limited to these compounds. Binding preferably takes place in the presence of an alcohol. Short-chain, branched or linear alkanols with one to five carbon atoms such as, for example, methanol, ethanol, propanol, isopropanol, butanols or pentanols are preferred. The concentration of the alkanols varies in a range from 1 to 100% (volume/volume), preferably from 2 to 80%, more preferably from 5 to 70%, still more preferably from 10 to 60% and most preferably from 15 to 50%. Surprisingly it has emerged that heating the solution containing the nucleic acid particularly in the presence of chaotropic reagents and alcohols exercises a similar influence both on the binding of viral RNA and DNA and on that of synthetic RNA and other nucleic acid species.

For the isolation of the nucleic acids the sample is brought into contact with the support material, preferably the above mentioned particles, and incubated for a time sufficient for binding. The incubation times for nucleic acids can be suitably between 10 seconds and 30 minutes. In practice incubation times in a range of $11\pm-10$ minutes have proved advantageous.

Silanised magnetic particles that are beaded or spherical and have a particle size in the range from 5 to 25 µm, preferably from 6 to 15 µm and particularly preferably from 6 to 10 µm and a very narrow size distribution, are preferred for the isolation of the nucleic acids. Magnetic silica particles that can be used advantageously in the method according to the invention are described in the international patent application WO 01/71732 page 6, line 29 to page 8, line 22, to which reference is made hereby in all points. According to the invention the binding takes place thereby in a temperature range from 36 to 75° C., preferably 46 to 70° C., particularly preferably 50 to 65° C. and most especially preferably at 56° C.

Similar effects on binding of nucleic acids are shown by i.a. denaturing substances such as, for example, dimethylsulphoxide.

Separation of the biological materials, preferably the nucleic acids from the sample liquid, is carried out after incubation. This is generally achieved by the separation of the nucleic acids bound to the particles according to the invention—with the use of magnetic silica particles—with the aid of a magnetic field. For example, the magnetic particles can be attracted to the walls of the vessel in which the incubation had taken place. Following this the liquid with the contents of the sample that were not bound to the magnetic particles is removed.

This removal depends upon the type of vessel in which the incubation has taken place. Suitable methodological steps for the removal of liquids are, for example, pipetting off or sucking off the liquid.

If desired, the loaded—magnetic—particles can be purified once or several times with a wash solution. The wash solution is selected such that a release of the biological material, e.g. the nucleic acids, from the particle surface preferably does not take place—or at least not in any significant amount—yet any impurities present are washed out as well as possible. This washing step preferably takes place by incubation of the wash solution with the loaded particles wherein preferably a resuspension of the particles is carried out, e.g. by shaking or application of a magnetic field not identical to the first magnetic field. The contaminated wash solution is preferably removed in the same manner as the lysate liquid at the end of the binding of the nucleic acids.

Any conventional wash buffer or any other suitable medium can be used as wash solution. Generally buffers with low or moderate ionic strength are preferred such as, for example, 10 mM Tris-HCl at a pH of 8, 0-10 mM NaCl. In addition, however, wash buffers that have higher salt concentrations—such as, for example, 3M guanidinium hydrochloride—can also be used. Equally, other standard media for carrying out the washing step can be used, for example alcohol containing media such as, for example, solutions of lower alkanols with one to five carbon atoms, preferably solutions of ethanol in water and especially preferred aqueous 70% ethanol.

The use of magnetic particles permits simple operation of washing steps by means of magnetic aggregation of the particles, separation of the nucleic acid binding medium, removal of the wash medium and addition of fresh wash medium as often as appears necessary to the person skilled in the art.

After the procedure for nucleic acid isolation and any optionally desired washing step, the carrier carrying the nucleic acid can be transferred, e.g. resuspended or immersed, into any suitable medium, e.g. water or a buffer with low ionic strength.

A short drying step of the magnetic particles in a vacuum or by stripping the liquid can be carried out after the last washing step.

It is of course obvious that the above-described steps of washing and drying are not only suitable for the purification and/or isolation of nucleic acids, but also for the purification and/or isolation of other above-mentioned biological materials.

Depending on the carrier and the nature of a subsequent work-up it can be desirable to elute the nucleic acids from the carrier or not to elute them from the carrier. In the case of a special solid carrier, such as the above-described magnetic particles, they can in many cases be used directly, for example in PCR or other amplification methods without the nucleic acids having to be eluted from the carrier. Furthermore, elution also is not necessary for many DNA detection methods or DNA identification methods, since although the DNA happens by chance to be in contact with the surface of the spheres and can be bound at a number of locations by hydrogen bonds or ionic bonds or other forces, a sufficient length of DNA is available for hybridisation with oligonucleotides and for amplification.

In the case where the biological material is a native nucleic acid, the nucleic acid can be removed from the magnetic particles according to the invention with an elution buffer of low salt content. Such buffers are known from the prior art [Analytical Biochemistry 175, 196-201 (1988)]. Buffers with a salt content of less than 0.1 mol/l are particularly used as elution buffers with a low salt content. Particularly preferably the elution buffer contains Tris-HCl.

Deionised water is also especially suitable for elution.

If desired, it is also possible to remove the RNA from the DNA, which can be achieved by destruction of the RNA prior to the DNA separation step, for example by the addition of RNase or alkali, e.g. NaOH.

By combination of the isolation of cells according to the invention described above with the isolation of nucleic acids according to the invention likewise described, preferably by binding in their native form to magnetic carrier materials, preferably in particle form, at the elevated binding temperature according to the invention a particularly advantageous method for the isolation of nucleic acids from cell samples is provided. The advantages of this embodiment do not only lie in its simplicity and high sensitivity as well as it being easily automated but in particular in a high yield through the binding according to the invention of the nucleic acids to silica surfaces at elevated temperatures.

As a result of the method according to the invention, isolated biological material can now be used further in any desired manner. For example, it can be used as substrate for different enzymatic reactions. In the case of nucleic acids mentioned by way of example are sequencing, radioactive or non-radioactive tagging, the amplification of one or more sequences contained therein, transcription, hybridisation with tagged probe nucleic acids, translation or ligation. One advantage of the method according to the invention is that the separation of biological material, in particular nucleic acids, from the liquid is not only simple, but can also be carried out with high yields and high throughput.

FIG. 1 shows mean values of the Ct values of HCV-RNA after real time (RT)-PCR in relation to the binding temperature. A further description of the illustration is found in Example 1.

Figure 2A:
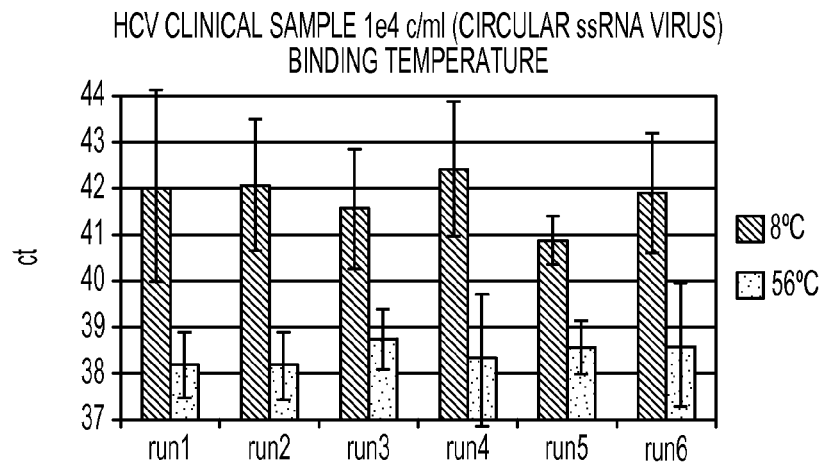
FIG. 2 shows mean values of the Ct values of HCV-RNA (FIG. 2a) HBV-DNA (FIG. 2b) and 'armored-HIV' (FIG. 2c) after real time (RT)-PCR in relation to the binding temperature. Negative human plasma with HCV (a single stranded RNA virus) and HBV (a double stranded DNA virus) as well as 'armored-HIV' (a synthetic RNA packed into a protein jacket) were treated according to the methodology described in Example 2. Each of 6 runs with in each case 6 replicates of the samples were treated on the one hand with a standard QIAGEN® MagAttract® Virus Mini M 48 protocol (protocol as in Example 1, but binding of the nucleic acids at 8° C.), and a modified MagAttract® Virus Mini M 48 protocol in which the lysate was tempered to 56° C. prior to binding. The eluates obtained were in each case subjected to a real time (RT)-PCR specific for HCV, HBV, and HIV.
Figure 2B:
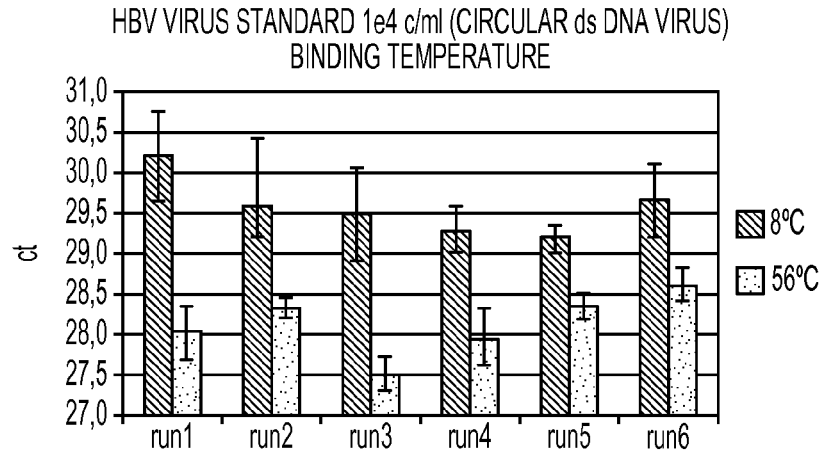
Figure 2C:
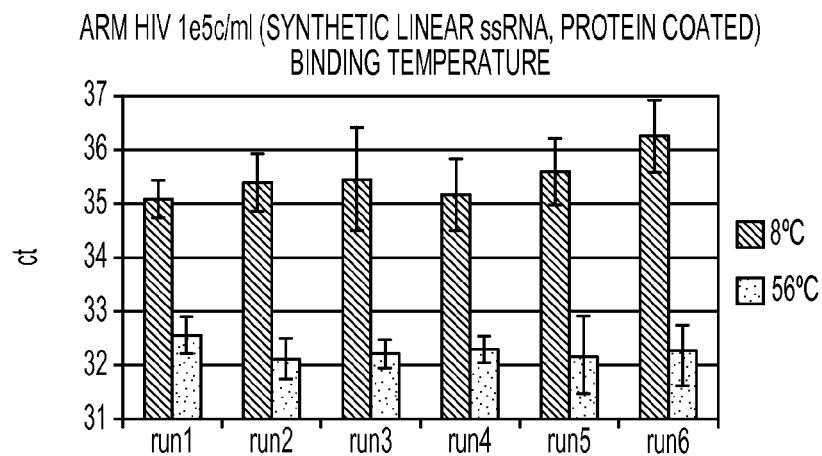

FIG. 2 shows mean values of the Ct values of HCV-RNA (FIG. 2a)) HBV-DNA (FIG. 2b)) and 'armored-HIV' (FIG. 2c)) after real time (RT)-PCR in relation to the binding temperature. A further description of the illustration is found in Example 2.

EXAMPLE 1

Extraction of viral RNA and viral DNA (carried out with the MagAttract™ Virus mini M 48 kit (QIAGENT™, Hilden, Deutschland).

400 μl plasma, serum or CSF (liquor) are treated with a commercially available lysis buffer, e.g. 435 μl QIAGEN™ lysis buffer AL containing 3 μg carrier-RNA, and a protease, e.g. 80 μl lyophilised QIAGEN™ protease, resuspended in QIAGENT™ Protease Resuspension Buffer, and mixed. The mixture is incubated for a period of 15 min at a temperature of 56° C.

Magnetic silica particles—e.g. 30 μl MagAttract™ Suspension B (QIAGEN, Hilden, Deutschland)—and 525 μl isopropanol are then added. A 5 minute incubation at 8° C., 18°

C., 26° C., 36° C., 46° C., 56° C., 65° C. or 75° C. (see below) then follows, during which the nucleic acids bind to the magnetic silica particles. After separation of the particles the liquid phase is removed and the particles are washed with a wash buffer, e.g. with 500 µl QIAGENT™ Wash Buffer AW 1 reconstituted with ethanol. After separation of the particles the liquid phase is removed and the particles are again washed—e.g. with 500 µl QIAGENT™ Wash Buffer AW 2 reconstituted with ethanol. The latter washing step is repeated. The particles are then washed with 500 µl ethanol. After separation of the particles the ethanolic phase is removed and the particles are dried at room temperature. Next the nucleic acids are eluted with a commercially available elution buffer—e.g. with 100 µl QIAGENT™ AVE Elution Buffer—the magnetic silica particles are removed and the eluate is heated over a period of 5 minutes to a temperature of 75° C.

Negative human plasma with HCV (RNA virus) was treated according to the above method. Each of 12 replicates of the samples were tempered prior to binding to 8° C., 18° C., 26° C., 36° C., 46° C., 56° C., 65° C. and 75° C., respectively. The eluates obtained were in each case subjected to an HCV-specific real-time (RT)-PCR. It is clearly seen from the mean values of the Ct values relative to binding temperature shown in FIG. 1 that using the methodology according to the invention during the binding over a temperature range of 36° C. to 75° C., the object forming the basis of the invention is impressively solved.

EXAMPLE 2

In a further experiment negative human plasma with HCV (a single stranded RNA virus) and HBV (a double stranded DNA virus) as well as 'armored-HIV' (a synthetic RNA packed into a protein jacket) were treated according to the methodology described in the above example.

Each of 6 runs with in each case 6 replicates of the samples were treated on the one hand with a standard QIAGEN MagAttract Virus Mini M 48 protocol (protocol as in Example 1, but binding of the nucleic acids at 8° C.), and a modified MagAttract Virus Mini M 48 protocol in which the lysate was tempered to 56° C. prior to binding. The eluates obtained were in each case subjected to a real time (RT)-PCR specific for HCV, HBV and HIV. From the mean values of the Ct values in relation to the binding temperature represented in FIG. 2a) to c) it is quite clear that when using the methodology according to the invention the binding of the nucleic acids at elevated temperature significantly increases the yield.

The invention claimed is:
1. In a method for the isolation and/or purification of a nucleic acid comprising:
  a) lysis of a biological sample,
  b) immobilization of a released nucleic acid on a matrix having one or more silicon-oxygen compounds in the presence of a chaotropic compound and a branched or linear alkanol,
  (c) separation of the bound nucleic acid from said sample, and wherein and optionally washing the nucleic acid immobilized on the matrix following step (b)
  the improvement comprises immobilization of the nucleic acid at a temperature range of 46° C. to 75° C.
2. The method according to claim 1, wherein the immobilization is carried out at a temperature in the range of 50° C. to 65° C.
3. The method according to claim 2, wherein the immobilization is carried out at a temperature of 56° C.
4. The method according to claim 1, wherein the silicon-oxygen compound comprises silica.
5. The method according to claim 1, wherein the matrix is represented by magnetic particles having a silica surface.
6. The method according to claim 1, wherein the chaotropic compound comprises a chaotropic sodium or guanidinium salt.
7. The method according to claim 6, wherein the chaotropic sodium or guanidinium salt is sodium iodide, sodium perchlorate, guanidinium thiocyanate, guanidinium isothiocyanate or guanidinium hydrochloride or a mixture thereof.
8. The method according to claim 1, wherein the branched or linear alkanol comprises an alcohol with one to five carbon atoms.
9. The method according to claim 8, wherein the alcohol comprises methanol, ethanol, isopropanol or a branched or linear butanol or pentanol or a mixture thereof.
10. The method according to claim 8 wherein the alkanol is present in the form of an aqueous solution in a concentration from 1 to 100% volume/volume.
11. The method accordign to claim 1, comrpising after step (b):
  washing the nucleic acid immobilized on the matrix.
12. The method of claim 11, wherein said biological sample is selected from the group consisting of body fluid, blood, plasma, urine, a tissue sample, and cells.
13. The method of claim 11, wherein said biological sample comprises viruses, phages, and/or cells.
14. The method of claim 1, wherein said biological sample is selected from the group consisting of body fluid, blood, plasma, urine, a tissue sample, and cells.
15. The method of claim 1, wherein the isolation and/or purification yield of a nucleic acid is increased when immobilization of the nucleic acid is carried out at a temperature range of 46° C. to 75° C. as compared to when immobilization of the nucleic acid is carried out at a temperature of 26° C.
16. The method of claim 1 comprising:
  a) lysis of a biological sample, wherein said biological sample is selected from the group consisting of body fluid, blood, plasma, urine, a tissue sample, and cells;
  b) immobilization of a released nucleic acid on a matrix having one or more silicon-oxygen compounds comprising silica in the presence of a chaotropic compound, wherein the chaotropic compound comprises a chaotropic sodium or guanidinium salt, and a branched or linear alkanol, wherein the branched or linear alkanol comprises an alcohol with one to five carbon atoms, and optionally washing the nucleic acid immobilized on the matrix,
  (c) separation of the bound nucleic acid from said sample, wherein immobilization of the nucleic acid is carried out at a temperature range of 46° C. to 75° C.
17. The method of claim 1, wherein said biological sample comprises viruses, phages, and/or cells.
18. In a method for the immobilization of a nucleic acid on a matrix having a silicon-oxygen compound in the presence of a chaotropic agent and a branched or linear alkanol, the improvement comprising immobilization of the nucleic acid is carried out in a temperature range of 46° to 75° C.
19. The method according to claim 18, wherein the immobilization on a matrix with a silica surface is carried out in the presence of a branched or linear alkanol of one to five carbon atoms or an aqueous solution thereof at a temperature in a range of 46° C. to 75° C.
20. The method according to claim 19, wherein the immobilization is carried out in the presence of methanol, ethanol, propanol, isopropanol, and/or a branched or linear butanol or pentanol or in the presence of an aqueous solution of an alcohol or a mixture thereof at a temperature in a range of 50° C. to 65° C.

21. The method according to claim 20, wherein the immobilization is carried out in the presence of an aqueous solution of methanol, ethanol, propanol and/or isopropanol in a concentration range of from 1 to 100% volume/volume at a temperature of 56° C.

22. The method according to claim 18, wherein the chaotropic compound is embodied by a chaotropic sodium or guanidinium salt.

23. The method according to claim 22, wherein the chaotropic sodium or guanidinum salt is at least one of sodium iodide, sodium perchlorate, guanidinium thiocyanate, guanidinum isothiocyanate or guanidinium hydrochloride.

24. The method according to claim 18, wherein the immobilization is carried out at a temperature in a range of 50° C. to 65° C.

25. The method according to claim 24, wherein the immobilization is carried out a temperature of 56° C.

26. The method according to claim 18, wherein the matrix is represented by magnetic particles with a silica surface.

27. The method of claim 18, further comprising washing the nucleic acid immobilized on the matrix.

* * * * *